US012715123B1

(12) United States Patent
Asadullah et al.

(10) Patent No.: US 12,715,123 B1
(45) Date of Patent: Aug. 25, 2026

(54) THREE-DIMENSIONAL RECONSTRUCTION OF INTERIORS OF CLOSED CONTAINERS

(71) Applicant: Infosys Limited, Bangalore (IN)

(72) Inventors: Allahbaksh Mohammedali Asadullah, Hubballi (IN); Monirul Islam, Bengaluru (IN); Hitesh C, Bengaluru (IN); Anant Pande, Bengaluru (IN); Trijeet Kr Modak, Kolkata (IN); Amirul Islam, Bengaluru (IN)

(73) Assignee: Infosys Limited, Bangalore (IN)

( * ) Notice: Subject to any disclaimer, the term of this patent is extended or adjusted under 35 U.S.C. 154(b) by 0 days.

(21) Appl. No.: 19/090,199

(22) Filed: Mar. 25, 2025

(51) Int. Cl.

| | |
|---|---|
| ***B25J 9/16*** | (2006.01) |
| ***A61L 2/10*** | (2026.01) |
| ***B65G 35/00*** | (2006.01) |

(52) U.S. Cl.
CPC ................. *B25J 9/163* (2013.01); *A61L 2/10* (2013.01); *B25J 9/1679* (2013.01); *B65G 35/00* (2013.01); *A61L 2202/11* (2013.01)

(58) Field of Classification Search
CPC . B25J 9/163; B25J 9/1679; A61L 2/10; A61L 2202/11; B65G 35/00; B62D 57/024; H01F 7/0242; B61B 13/00; B61B 15/00; A63H 18/00; A63H 19/00
See application file for complete search history.

(56) References Cited

U.S. PATENT DOCUMENTS 7,154,363 B2 12/2006 Hunts
8,522,905 B2 9/2013 Lama
9,129,251 B2 * 9/2015 Davidson ............. G06Q 10/087
9,345,979 B2 * 5/2016 Matthes ................. A63H 18/06
9,586,636 B1 3/2017 Burmeister et al.

(Continued)

FOREIGN PATENT DOCUMENTS

WO WO-2021121016 A1 * 6/2021 ............. B25J 19/00

OTHER PUBLICATIONS

Wael Saab et al., "A review of coupling mechanism designs for modular reconfigurable robots", Oct. 11, 2018, Robotica (2019) vol. 37, pp. 378-403, Cambridge University Press 2018, DOI: 10.1017/S0263574718001066.

(Continued)

*Primary Examiner* — Robert T Nguyen
(74) *Attorney, Agent, or Firm* — Finnegan, Henderson, Farabow, Garrett & Dunner, LLP

(57) ABSTRACT

A system for three-dimensional (3D) reconstruction of interiors of a closed container (e.g., a refrigerator) is provided. A track is mounted inside the refrigerator. A robot is configured to navigate along the track. The robot may include control modules and puller and pusher modules that are magnetically coupled to the control modules. The puller module may pull the control modules along the track, whereas the pusher module may push the control modules along the track. Each control module may include an image sensor that captures images of the physical space inside the refrigerator. The track is mounted such that by navigating along the track, the robot (e.g., the image sensors) can capture an entire scene of a physical space inside the refrigerator from different angles and locations within the refrigerator. Based on the captured images, a 3D representation of the physical space is generated.

20 Claims, 8 Drawing Sheets

(56) References Cited

U.S. PATENT DOCUMENTS

2024/0277429 A1* 8/2024 Moll ...................... A61B 50/10

OTHER PUBLICATIONS

Joshua Elliott et al., “Mobility Modes and Control of a Passively-Articulated Multi-Segment Wheeled Vehicle”, Proceedings of the ISTVS 20th International and 9th Americas Conference, Sep. 27-29, 2021.

Tiange Xue et al., “A New Magnetic Coupling Mechanism for Patrol Robot Wireless Charging System”, Oct. 2020, Journal of Physics Conference Series, DOI: 10.1088/1742-6596/1639/1/012067.

“How is the high current pogo pins used on the industrial robot”, Jun. 2024, Technology News, Smeconn, https://smeconn.com/how-is-the-high-current-pogo-pins-used-on-the-industrial-robot/.

“What Makes Pogo Pins Essential in Modern Electronics?”, Nov. 14, 2024, Talk Android, https://www.talkandroid.com/494304-what-makes-pogo-pins-essential-in-modern-electronics/.

* cited by examiner

THREE-DIMENSIONAL RECONSTRUCTION OF INTERIORS OF CLOSED CONTAINERS

FIELD OF THE DISCLOSURE

Various embodiments of the present disclosure relate generally to three-dimensional reconstructions. More specifically, various embodiments of the present disclosure relate to the three-dimensional reconstruction of interiors of closed containers.

BACKGROUND

A refrigerator is an electronic appliance engineered to preserve perishable goods by consistently maintaining low temperatures that slow bacterial growth and extend the freshness of items like dairy, meat, fruits, or the like. Modern refrigerators are equipped with specialized compartments and smart storage solutions that create optimal conditions for different food types. In today's fast-paced lifestyle, especially for busy working professionals, keeping track of what is inside the refrigerator becomes a challenge. Without efficient inventory management, consumers may inadvertently repurchase items they already have, overlook essentials that need restocking, or allow food to expire unnoticed. This lack of visibility not only contributes to significant food waste and increased costs but also complicates meal planning.

In light of the foregoing, there exists a need for a technical and reliable solution that overcomes the abovementioned problems.

Limitations and disadvantages of conventional and traditional approaches will become apparent to one of skill in the art, through the comparison of described systems with some aspects of the present disclosure, as set forth in the remainder of the present disclosure and with reference to the drawings.

SUMMARY

Methods and systems for three-dimensional (3D) reconstruction of interiors of closed containers are provided substantially as shown in, and described in connection with, at least one of the figures.

In an embodiment of the present disclosure, a system is disclosed. The system includes a housing encompassing a physical space. The housing includes a plurality of walls. The system further includes a track mounted on the plurality of walls, and a robot configured to navigate along the track. The robot includes a set of control modules, a puller module, and a pusher module. The puller module is magnetically coupled to the set of control modules, and configured to pull the set of control modules along the track. The pusher module is magnetically coupled to the set of control modules, and configured to push the set of control modules along the track. While navigating along the track, the set of control modules is configured to capture an input dataset. The input dataset includes a plurality of images associated with each of a plurality of objects present in the physical space. Further, a 3D representation of the physical space is derived based on the input dataset.

In some embodiments, the track corresponds to a continuous rail mounted on the plurality of walls in a horizontal direction and a vertical direction.

In some embodiments, the housing further includes a set of trays arranged within the physical space in contact with the plurality of walls. The plurality of objects are positioned on the set of trays.

In some embodiments, the track is further mounted on a bottom surface of at least one of the set of trays.

In some embodiments, the set of control modules includes a first control module, a second control module, and a third control module that are magnetically coupled in series. The first control module is further magnetically coupled to the puller module, and the third control module is further magnetically coupled to the pusher module.

In some embodiments, each of the set of control modules includes a magnet mounted on a base of a corresponding control module. The magnet facilitates alignment of each of the set of control modules along the track during the navigation of the robot.

In some embodiments, the puller module includes (i) a first set of wheels, (ii) a first set of motors configured to drive the first set of wheels along the track, and (iii) a first set of magnets that is magnetically coupled to a first control module of the set of control modules. Based on the driving of the first set of wheels and the magnetic coupling of the first set of magnets to the first control module, the set of control modules is pulled along the track. The pusher module includes (i) a second set of wheels, (ii) a second set of motors configured to drive the second set of wheels along the track, and (iii) a second set of magnets that is magnetically coupled to a second control module of the set of control modules. Based on the driving of the second set of wheels and the magnetic coupling of the second set of magnets to the second control module, the set of control modules is pushed along the track.

In some embodiments, the puller module includes a first set of magnets, and the pusher module includes a second set of magnets. The set of control modules includes (i) a first control module that includes a third set of magnets that is magnetically coupled to the first set of magnets, and (ii) a second control module that includes a fourth set of magnets that is magnetically coupled to the second set of magnets. The robot navigates along the track based on (i) a magnetic attraction between the first set of magnets and the third set of magnets and (ii) a magnetic repulsion between the second set of magnets and the fourth set of magnets.

In some embodiments, the track includes a conductive rail. Each of the set of control modules, the puller module, and the pusher module comprises (i) a set of components and (ii) a set of pogo pins that is coupled to the track and the set of components, and configured to draw power from the track and supply the drawn power to the set of components.

In some embodiments, the housing further comprises a roof and a base. The track is mounted further on the roof and the base.

In some embodiments, each of the set of control modules includes one or more sensors configured to generate sensing data. The input dataset includes the sensing data generated by the one or more sensors of each of the set of control modules. Each of the set of control modules further includes a communication unit that is communicatively coupled to the one or more sensors, and configured to facilitate communication of the sensing data to one or more components that are external to the robot.

In some embodiments, the one or more sensors comprise an image sensor configured to capture a set of images of the plurality of images.

In some embodiments, each of the set of control modules further comprises a rotating mount. The image sensor is mounted on the rotating mount.

In some embodiments, the sensing data, generated by the one or more sensors of each of the set of control modules, further comprises at least one of temperature sensing data indicative of a temperature of the physical space, gas sensing data indicative of air quality of the physical space, or audio sensing data indicative of acoustic characteristics of the physical space.

In some embodiments, the one or more sensors, of each of the set of control modules, comprise at least one of a temperature sensor configured to capture the temperature sensing data, a gas sensor configured to capture the gas sensing data, or an audio sensor configured to capture the audio sensing data.

In some embodiments, each of the set of control modules comprises an ultraviolet light source that is configured to sanitize the housing.

In some embodiments, the system further comprises a processing device that is communicatively coupled to the set of control modules, and configured to obtain the input dataset, process the input dataset to determine the plurality of objects present in the physical space, and generate, using a 3D reconstruction model, the 3D representation of the physical space based on the processed input dataset.

In some embodiments, the 3D reconstruction model is trained based on a training dataset that comprises one or more images of one or more objects, respectively, that are associated with the system.

In some embodiments, the processing device is further configured to receive, from a user device, a user request that is indicative of visualization of the plurality of objects. The processing device generates the 3D representation of the physical space in response to the user request. The processing device is further configured to render the 3D representation of the physical space on the user device.

In some embodiments, to generate the 3D representation of the physical space, the processing device is further configured to detect, from the plurality of objects, at least a first object that is occluded, and reconstruct the first object using the 3D reconstruction model.

In some embodiments, the processing device is further configured to receive, from a user device, a user request indicative of detection of a first object of the plurality of objects, execute an object detection operation on the 3D representation to detect the first object, and provide one or more details associated with the first object to the user device.

In some embodiments, the processing device is further configured to monitor, based on the 3D representation, at least one of a type, a quantity, a quality, a color, or a texture associated with the plurality of objects.

In some embodiments, the housing further includes a door enclosing the plurality of walls. The robot navigates along the track based on one of (i) a closure of the door, (ii) a weight change event associated with the physical space, (iii) a lapse of a predefined time interval, or (iv) a user request.

In some embodiments, the housing corresponds to a refrigerator housing.

In some embodiments, the track is mounted on the plurality of walls such that based on the navigation along the track, the robot is configured to capture an entire scene of the physical space.

In another embodiment of the present disclosure, a robot is disclosed. The robot includes a set of control modules, a puller module, and a pusher module. The puller module is magnetically coupled to the set of control modules, and configured to pull the set of control modules along a track. The track is mounted on a plurality of walls of a housing encompassing a physical space. The pusher module is magnetically coupled to the set of control modules, and configured to push the set of control modules along the track. While navigating along the track, the set of control modules is configured to capture an input dataset. The input dataset includes a plurality of images associated with each of a plurality of objects present in the physical space. A 3D representation of the physical space is derived based on the input dataset.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

Embodiments of the present disclosure are illustrated by way of example and are not limited by the accompanying figures. Similar references in the figures may indicate similar elements. Elements in the figures are illustrated for simplicity and clarity and have not necessarily been drawn to scale.

DETAILED DESCRIPTION

Figure 1:
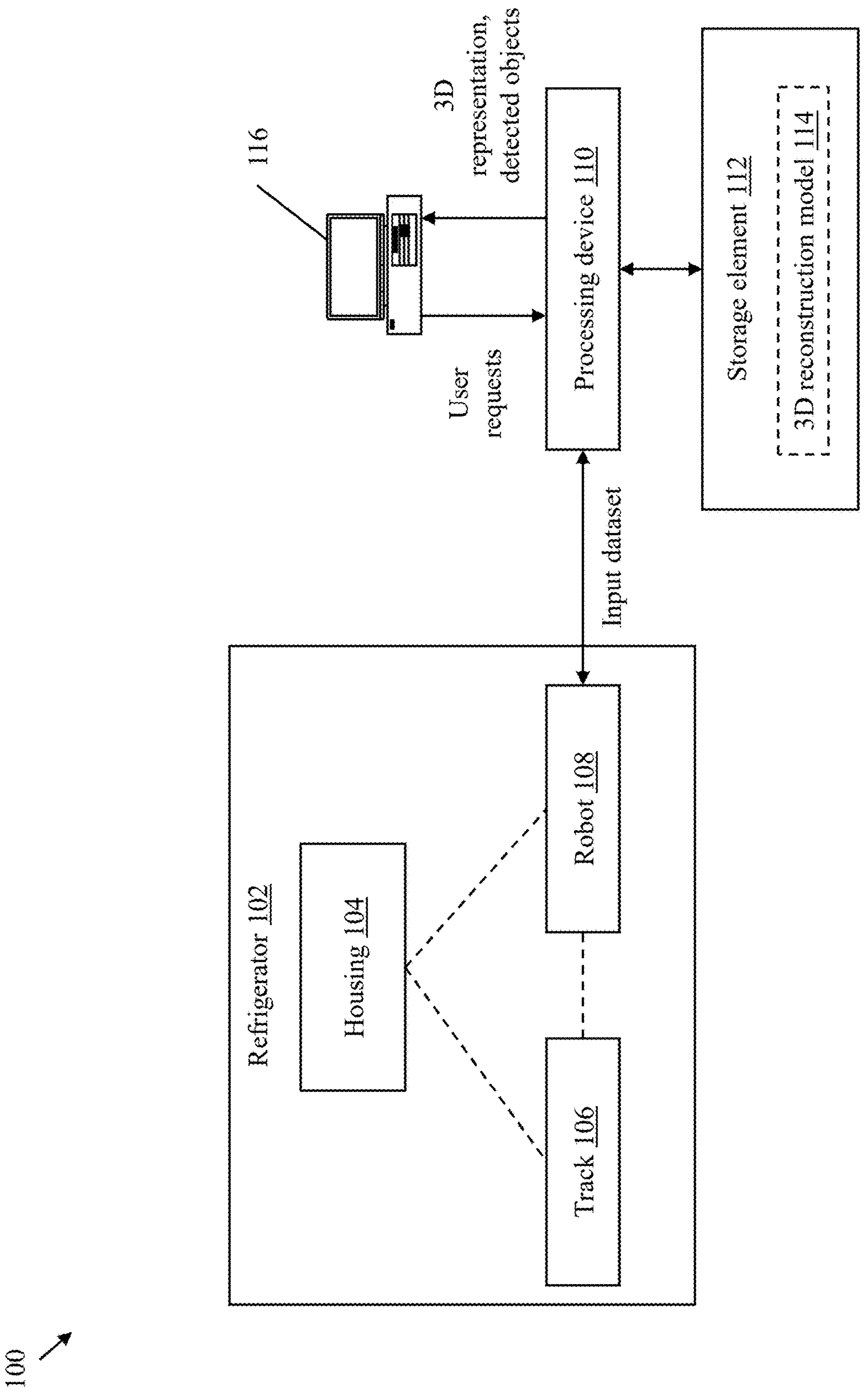
FIG. 1 is a schematic diagram that illustrates an environment for three-dimensional (3D) reconstruction of interiors of closed containers, consistent with disclosed embodiments of the present disclosure.

The detailed description of the appended drawings is intended as a description of the embodiments of the present disclosure and is not intended to represent the only form in which the present disclosure may be practiced. It is to be understood that the same or equivalent functions may be accomplished by different embodiments that are intended to be encompassed within the spirit and scope of the present disclosure.

Overview:

Conventionally, to alleviate the issues related to food waste, increased costs, and complicated meal planning, refrigerator contents may be monitored remotely. Remote monitoring of refrigerator contents leverages Internet-of-things (IoT) technologies, such as embedded cameras, weight sensors, and barcode scanners, integrated with image recognition algorithms, to automatically track and display what is inside a refrigerator via smartphone apps or cloud-connected interfaces. These systems aim to simplify inventory management by notifying users when supplies run low, suggesting shopping lists, or even integrating with online grocery services to automate replenishment. The goal is to reduce food waste, avoid duplicate purchases, and streamline meal planning by providing real-time data on the status of perishable goods.

The remote monitoring solutions, however, come with notable shortcomings. Camera-based remote monitoring systems often struggle to provide a complete and accurate view due to poor and varying lighting conditions inside the refrigerator and reflections from glossy surfaces. Additionally, the cluttered and constantly changing arrangement of items can lead to occlusions, where some items block the view of others, resulting in incomplete data capture. These factors make it difficult for image recognition algorithms to reliably identify and inventory all the contents, leading to potential inaccuracies in identification, tracking, and notifications. While alternative solutions like weight sensors and scanners are sometimes used to complement camera-based monitoring, they too have limitations. Weight sensors may register the presence of items without offering detailed information about what they are, and scanners require every product to be tagged correctly, which may not always be practical or consistently maintained by users.

The present disclosure addresses these limitations by providing a system for three-dimensional (3D) reconstruction of the interiors of a closed container (e.g., the refrigerator). A track may be mounted on the interior walls of the refrigerator and on the bottom surfaces of trays present within the refrigerator. The track may be a continuous rail mounted in a horizontal direction and a vertical direction. Further, a robot may be configured to navigate along the track. The track may be mounted such that based on the navigation along the track, the robot may be configured to capture an entire scene of a physical space inside the refrigerator. The robot may include various control modules and puller and pusher modules that are magnetically coupled to the control modules. The puller module may pull the set of control modules along the track, whereas the pusher module may push the control modules along the track. The robot may navigate along the track based on a magnetic attraction between the puller module and the control modules, and a magnetic repulsion between the pusher module and the control modules.

Each control module may include various sensors configured to capture sensing data. For example, each control module may include at least one image sensor to capture two-dimensional (2D) images of the physical space inside the refrigerator. The robot may navigate in a manner that the image sensor may capture the images from different angles and different locations within the refrigerator. Based on the images captured by the image sensor, a 3D representation of the physical space inside the refrigerator may be generated. The generation of the 3D representation may involve reconstruction of partially or fully obscured objects using a 3D reconstruction model that is trained based on images of items likely to be present in the refrigerator. The 3D representation may be rendered on a user device of a user to present the entire scene inside the refrigerator to the user. Additionally, the 3D representation may be utilized to provide details of various items inside the refrigerator. Further, the 3D representation may be utilized to monitor a type, a quantity, a quality, a color, or a texture associated with the items present inside the refrigerator.

The present disclosure thus provides a solution to accurately capture and reconstruct the interiors of a closed container (e.g., the refrigerator). The solution can be retrofitted to conventional refrigerators, thereby making the system cost-effective and compatible. Further, as the images of the interiors of the refrigerator are captured from different angles and locations, the accuracy of the 3D representation is significantly greater than conventional systems which may use a fixed camera to capture images. Additionally, the reconstruction of occluded items provides a more detailed and accurate 3D representation and addresses the challenge of accurately detecting and localizing objects within the refrigerator. The 3D reconstruction of the present disclosure is thus less sensitive to changes in the lighting conditions and occlusions as compared to the conventional systems. The present disclosure may thus allow detailed and accurate representations of the interiors of the refrigerator that can be utilized for automatically tracking inventory, thereby allowing the user to manage the inventory efficiently and avoid food wastage.

Figure Description:

FIG. 1 is a schematic diagram that illustrates an environment 100 for three-dimensional (3D) reconstruction of interiors of closed containers, consistent with disclosed embodiments of the present disclosure. The environment 100 may include a refrigerator 102. The refrigerator 102 may be an electronic appliance engineered to preserve perishable goods by consistently maintaining low temperatures that slow bacterial growth and extend the freshness of items like dairy, meat, fruits, or the like. The refrigerator 102 may include a housing 104. The housing 104 may correspond to a refrigerator housing. The housing 104 may refer to an enclosure encompassing a physical space within the refrigerator 102. The housing 104 may include a plurality of walls, a roof, a base, and a door enclosing the plurality of walls, the roof, and the base. Additionally, the housing 104 may include a set of trays arranged within the physical space in contact with the plurality of walls. Various objects may be positioned on the set of trays inside the refrigerator 102. Examples of the objects may include vegetables, fruits, containers, and other perishable items.

Modern refrigerators feature specialized compartments and smart storage solutions to optimize food preservation, yet tracking their contents remains challenging for busy users. To address issues like food waste, increased costs, and complicated meal planning, remote monitoring systems have been developed, integrating embedded cameras, weight sensors, and barcode scanners with image recognition algorithms to provide real-time inventory updates via smartphone apps. However, these solutions are hindered by poor and variable lighting, reflections, and clutter-induced occlusions inside the refrigerators that impair accurate data capture. While there are alternatives like weight sensors and scanners, they either lack detailed information or depend on consistent tagging, reducing their overall effectiveness.

To overcome these challenges, a 3D reconstruction technique is disclosed in the present disclosure that generates accurate 3D representations of the interiors of the refrigerator 102. To facilitate the 3D reconstruction technique, the refrigerator 102 may include a track 106 that is mounted on the plurality of walls of the housing 104. The track 106 may correspond to a continuous rail mounted on the plurality of walls in a horizontal direction and a vertical direction. The track 106 may be further mounted on a bottom surface of at least one of the set of trays. The refrigerator 102 may further include a robot 108 that may be configured to navigate along the track 106. The track 106 may be mounted on the plurality of walls and the bottom surface of the trays such that based on the navigation along the track 106, the robot 108 may be configured to capture an entire scene of the physical space inside the refrigerator 102. The refrigerator 102, along with the track 106 and the robot 108, is explained in detail in conjunction with FIGS. 2A, 2B, 3A, and 3B.

While navigating along the track 106, the robot 108 may be configured to capture an input dataset. In an example, the input dataset comprises a plurality of images associated with each object present in the physical space. In other words, the robot 108 may capture two-dimensional (2D) images of the physical space inside the refrigerator 102. The robot 108 may navigate in a manner that images may be captured from different angles and different locations within the refrigerator 102.

The scope of the present disclosure is not limited to the input dataset comprising exclusively images. In several embodiments, the input dataset may include temperature sensing data indicative of a temperature of the physical space, gas sensing data indicative of air quality of the physical space, or audio sensing data indicative of acoustic characteristics of the physical space.

The input dataset may be utilized to generate a 3D representation of the physical space inside the refrigerator 102. The 3D representation may be utilized to monitor a type, a quantity, a quality, a color, or a texture associated with a plurality of objects present inside the refrigerator 102.

To facilitate the 3D reconstruction technique of the present disclosure, the environment 100 may further include a processing device 110. The processing device 110 may be communicatively coupled to the robot 108. The processing device 110 may include suitable logic, circuitry, interfaces, and/or code, executable by the circuitry, that may be configured to perform one or more operations. For example, the processing device 110 may be configured to obtain the input dataset from the robot 108. Further, the processing device 110 may be configured to process the input dataset to determine the plurality of objects present in the physical space. The processing device 110 may be further configured to generate the 3D representation of the physical space based on the processed input dataset.

Although it is described that the processing device 110 is external to the refrigerator 102, the scope of the present disclosure is not limited to it. In several embodiments, the processing device 110 may be integrated with the refrigerator 102 or may be mounted on the housing 104, without deviating from the scope of the present disclosure.

The environment 100 may further include a storage element 112 that is coupled to the processing device 110. The storage element 112 may correspond to a hardware storage (for example, hard drive, solid-state drive, or the like) or a cloud storage (for example, cloud services). The storage element 112 may be configured to store a 3D reconstruction model 114. The 3D reconstruction model 114 may utilize a combination of deep learning and computer vision techniques to synthesize data from multiple images and create a detailed high-quality digital replica of a scene inside the refrigerator 102. In an embodiment, the 3D reconstruction model 114 may be trained based on a training dataset that comprises one or more images of one or more objects, respectively, that are associated with the refrigerator 102. In other words, the 3D reconstruction model 114 may be trained based on the training dataset that includes images of objects likely to be present inside the refrigerator 102. Such training may enable the 3D reconstruction model 114 to recognize and distinguish between similar objects (e.g., different types of fruit or vegetables), which may be challenging for conventional computer vision algorithms. The processing device 110 may generate the 3D representation of the physical space based on the processed input dataset using the 3D reconstruction model 114. In an embodiment, the processing device 110 may store the generated 3D representation in the storage element 112.

The present disclosure may provide a solution to accurately capture and reconstruct interiors of a closed container (e.g., the refrigerator 102). The solution can be retrofitted to conventional refrigerators, thereby making the solution cost-effective and compatible. Further, as the images of the interiors of the refrigerator 102 are captured from different angles and locations, the accuracy of the 3D representation is significantly greater than conventional systems which may use a fixed camera to capture images.

In an embodiment, to generate the 3D representation of the physical space, the processing device 110 may be further configured to detect, from the plurality of objects, at least a first object that is occluded. Further, the processing device 110 may be configured to reconstruct the first object using the 3D reconstruction model 114. The reconstruction of occluded items provides a more detailed and accurate 3D representation and addresses the challenge of accurately detecting and localizing objects within the refrigerator 102.

The 3D reconstruction of the present disclosure is thus less sensitive to changes in the lighting conditions and occlusions as compared to conventional systems. Further, the 3D reconstruction of the present disclosure is a more scalable and cost-effective solution than existing solutions. The present disclosure may thus allow detailed and accurate representations of the interiors of the refrigerator 102 that can be utilized for automatically tracking inventory, thereby allowing the users to manage the inventory efficiently and avoid food wastage with significantly reduced manual intervention.

In an example, the processing device 110 may be configured to receive a first user request that is indicative of visualization of the plurality of objects inside the refrigerator 102. The environment 100 may further include a user device 116 that is coupled to the processing device 110. The user device 116 may correspond to a cellphone, a laptop, a tablet, a phablet, a desktop, a computer, or the like. The user device 116 may be associated with a user (not shown). The user device 116 may include suitable logic, circuitry, interfaces, and/or code, executable by the circuitry, that may be configured to perform one or more operations for interacting with the processing device 110. For example, the user device 116 may be used by the user to provide the first user request to the processing device 110. The processing device 110 may thus receive the first user request from the user device 116. Further, the processing device 110 may be configured to render the 3D representation of the physical space on the user device 116. The user is thus able to remotely visualize the interior of the refrigerator 102. In an embodiment, the processing device 110 may generate the 3D representation of the physical space in response to the first user request. In another embodiment, the processing device 110 may retrieve the 3D representation of the physical space stored in the storage element 112 in response to the first user request.

The first user request may not be limited to the visualization of all the objects present inside the refrigerator 102. In numerous embodiments, the first user request may be indicative of visualization of a section (e.g., a compartment) of the refrigerator 102. In such a scenario, the processing device 110 may be configured to determine the coordinates of the section requested in the first user request, and generate the 3D representation of the corresponding section for rendering on the user device 116.

In several embodiments, the processing device 110 may be further configured to receive, from the user device 116, a second user request indicative of detection of an object of the plurality of objects. The user device 116 may be used by the user to provide the second user request to the processing device 110. The processing device 110 may be further configured to execute an object detection operation on the 3D representation to detect the requested object. In an embodiment, the processing device 110 may generate the 3D representation of the physical space in response to the second user request. In another embodiment, the processing device 110 may retrieve the 3D representation of the physical space stored in the storage element 112 in response to the second user request. In some embodiments, the processing device 110 may retrieve the 3D representation from the storage element 112 when it is determined that the scene inside the refrigerator 102 has not changed since the previous 3D representation generation. The processing device 110 may be further configured to provide one or more details associated with the detected object to the user device 116. The one or more details associated with the detected object may include a type, a quantity, an expiration date, a brand, or the like, of the detected object.

The processing device 110 may be further configured to monitor, based on the 3D representation, at least one of a type, a quantity, a quality, a color, or a texture associated with the plurality of objects present inside the refrigerator 102. For example, the 3D representation may be utilized to detect and monitor changes in the condition of food items over time, such as changes in color or texture, or the presence of mold, which may be difficult to detect with existing solutions. This could help the user ensure that the products are safe for consumption. The safety can be measured based on the time the items are kept in the refrigerator 102 and also the approximate life of the item. For leafy vegetables, the safety can be measured using the color of the vegetables. Further, the 3D representation may be utilized to monitor the inventory of food items in the refrigerator 102, which could help the user manage inventory more efficiently. The 3D representation may also be utilized to monitor the quality and freshness of food items in the refrigerator 102, which could help the user ensure that the products meet quality standards. The 3D representation may also be utilized to monitor food items that are approaching their expiration date, which could help the user reduce food waste by consuming or selling these items before they expire. As the 3D representation may generate accurate 3D models of food items and their quantity in the refrigerator 102, a more detailed and accurate product information for online grocery shopping may be provided, which can be utilized to replenish stocks at appropriate intervals.

In some embodiments, based on the monitoring of the plurality of objects, the processing device 110 may be configured to generate alerts when items are running low or have expired.

In some embodiments, based on the 3D representation, the processing device 110 may be further configured to monitor and optimize the layout of objects inside the refrigerator 102 to reduce waste and improve energy efficiency by ensuring that the refrigerator 102 is operating at maximum efficiency.

In some embodiments, based on the 3D representation, the processing device 110 may be further configured to determine consumer behavior and preferences.

In numerous embodiments, the processing device 110 may be integrated with other smart home devices, such as virtual assistants, to provide the user with more intuitive and personalized experiences, such as remote tracking, auto reordering, and systematic alerts.

In several embodiments, the refrigerator 102 may include various other sensors (not shown). The 3D reconstruction technique of the present disclosure may be utilized in conjunction with these sensors to monitor the presence and location of objects within the refrigerator 102. The processing device 110 may be further configured to compare the generated 3D representation to sensor data sensed by these sensors to validate the identification and tracking of individual objects within the refrigerator 102.

Although the 3D reconstruction technique of the present disclosure is described for the refrigerator 102, the scope of the present disclosure is not limited to it. In several embodiments, the 3D reconstruction technique of the present disclosure may be implemented for various other closed containers (e.g., storage containers, wardrobes, or the like), without deviating from the scope of the present disclosure.

Figure 2A:
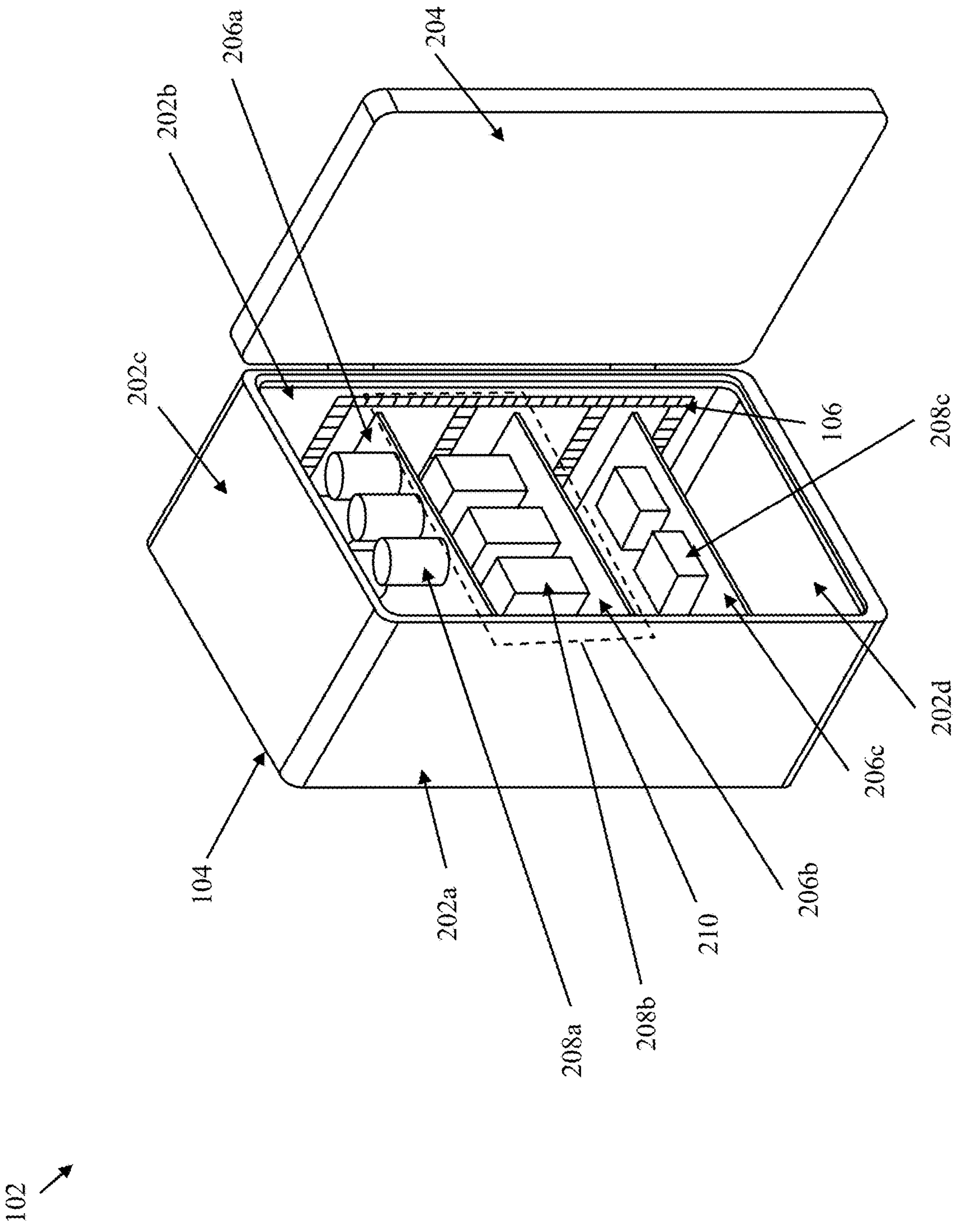
FIG. 2A is a schematic diagram that illustrates an isometric view of a refrigerator of the environment of FIG. 1, consistent with disclosed embodiments of the present disclosure.

FIG. 2A is a schematic diagram that illustrates an isometric view of the refrigerator 102, consistent with disclosed embodiments of the present disclosure. The refrigerator 102 may include the housing 104. The housing 104 may include a plurality of walls, of which walls 202*a* and 202*b* are shown. The walls 202*a* and 202*b* may correspond to the sides of the housing 104 (e.g., the refrigerator 102). The plurality of walls may further include a wall (not visible in FIG. 2A) connecting the walls 202*a* and 202*b*. The housing 104 may further include a roof 202*c* and a base 202*d*. The housing 104 may further include a door 204 enclosing the plurality of walls, the roof 202*c*, and the base 202*d*. The plurality of walls, the roof 202*c*, the base 202*d*, and the door 204 may thus encompass the physical space inside the refrigerator 102.

The housing 104 may further include a set of trays, of which trays 206*a*-206*c* are shown. The trays 206*a*-206*c* may be arranged within the physical space in contact with the plurality of walls. Various objects may be positioned on the trays 206*a*-206*c* inside the refrigerator 102. As illustrated in FIG. 2A, an object 208*a* is positioned on the tray 206*a*, an object 208*b* is positioned on the tray 206*b*, and an object 208*c* is positioned on the tray 206*c*. Other objects positioned on the trays 206*a*-206*c* are not labeled in FIG. 2A to keep the illustration concise and clear and should not be considered a limitation of the present disclosure.

As illustrated in FIG. 2A, the housing 104 may further include the track 106 that is mounted on the wall 202*b*. The track 106 may be a guiding structure designed to provide a stable surface for wheels thereby ensuring smooth movement. In an example, the track 106 may be made of metal or any other durable material to ensure controlled and efficient movement. Although not shown in FIG. 2A, the track 106 may also be mounted on the wall 202*a*, the roof 202*c*, and the base 202*d*, without deviating from the scope of the present disclosure. The track 106 may also be mounted on the bottom surface of at least one of the trays 206*a*-206*c*. In the refrigerator 102 shown in FIG. 2A, the track 106 may also be mounted on the bottom surface of the tray 206*a*. A compartment 210 of the housing 104 may thus include portions of the track 106 mounted on all three sides. A front view of the compartment 210 is illustrated in FIG. 2B.

Figure 2B:
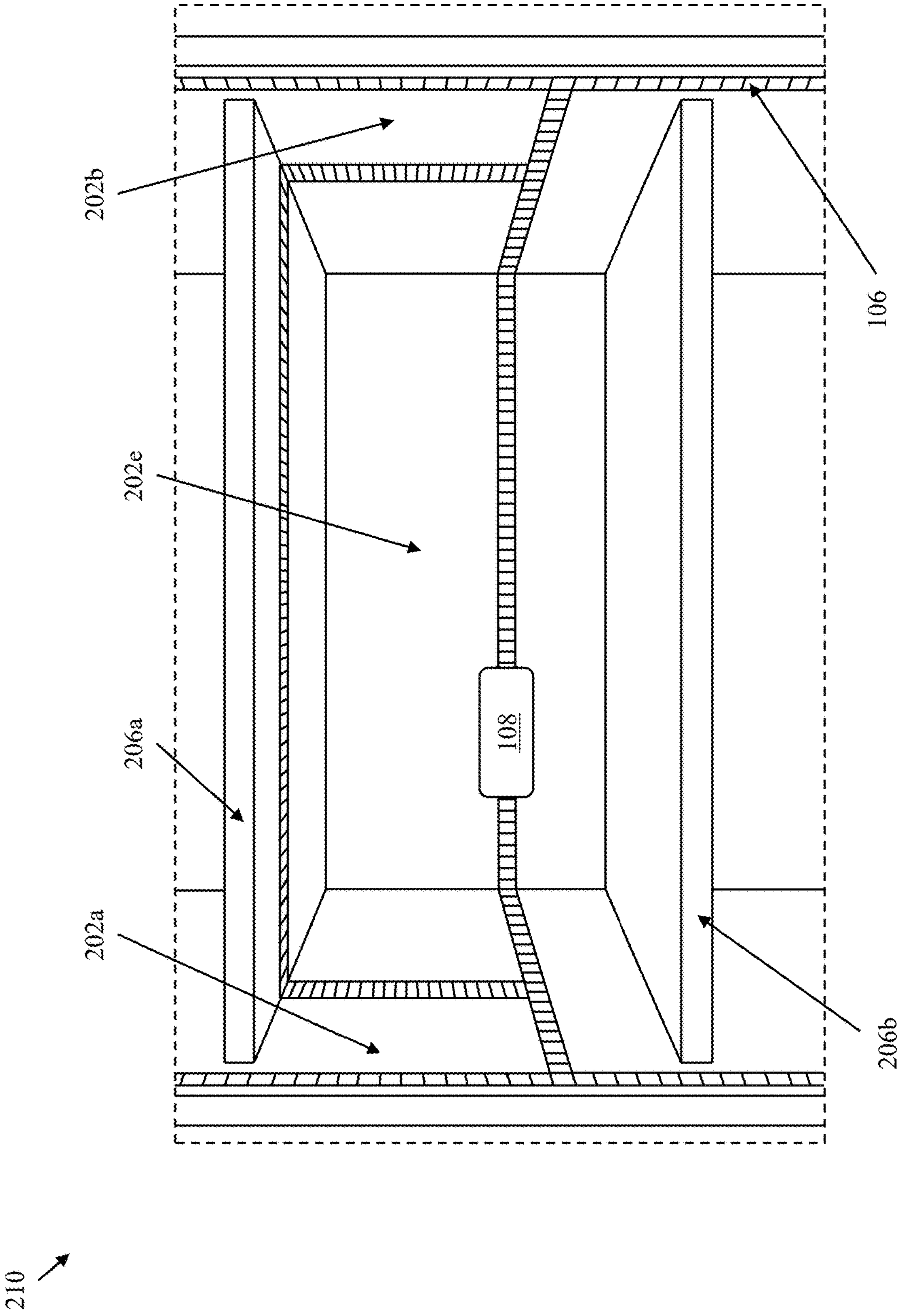
FIG. 2B is a schematic diagram that illustrates a front view of a compartment of the refrigerator of FIG. 2A, consistent with disclosed embodiments of the present disclosure.

FIG. 2B is a schematic diagram that illustrates the front view of the compartment 210, consistent with disclosed embodiments of the present disclosure. As shown in FIG. 2B, the track 106 is mounted along the wall 202*a*, the bottom surface of the tray 206*a*, the wall 202*b*, and a wall 202*e*. The wall 202*e* may be the wall connecting the walls 202*a* and 202*b*, and which was not visible in FIG. 2A.

The track 106 may correspond to a continuous rail mounted on the walls (e.g., the walls 202*a*, 202*b*, and 202*e*)

in a horizontal direction and a vertical direction. The continuous rail of the track 106 may thus facilitate movement of the robot 108 along the track 106. The arrangement of the track 106 in the compartment 210 is such that the robot 108 may be configured to capture the images that cover the entire interior space within the compartment 210. Further, the images may be taken from different angles to capture different perspectives of the objects inside the compartment 210.

Figure 3A:
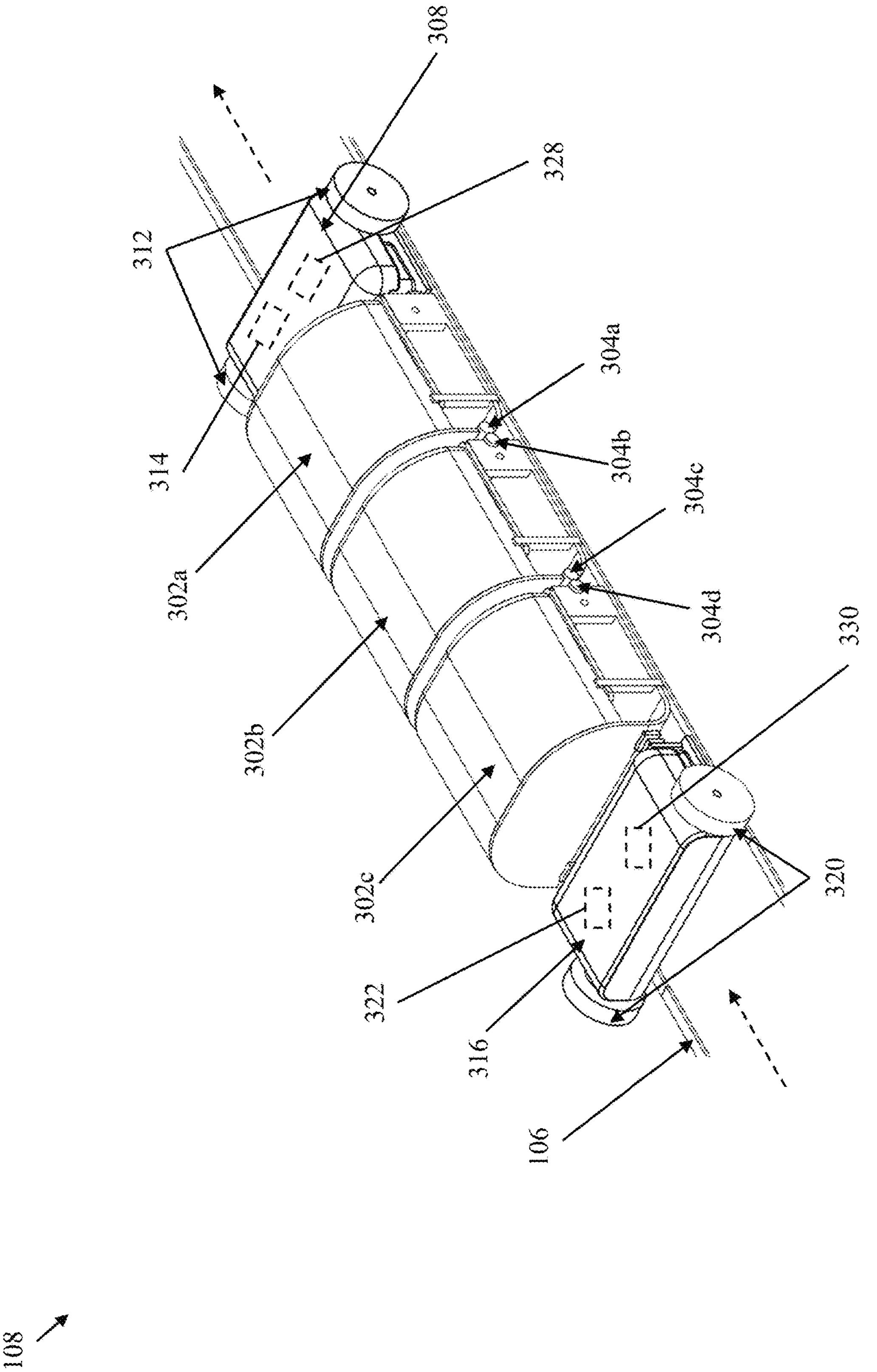
FIGS. 3A and 3B are schematic diagrams that illustrate an isometric view and a side view of a robot of the environment of FIG. 1, respectively, consistent with disclosed embodiments of the present disclosure.
Figure 3B:
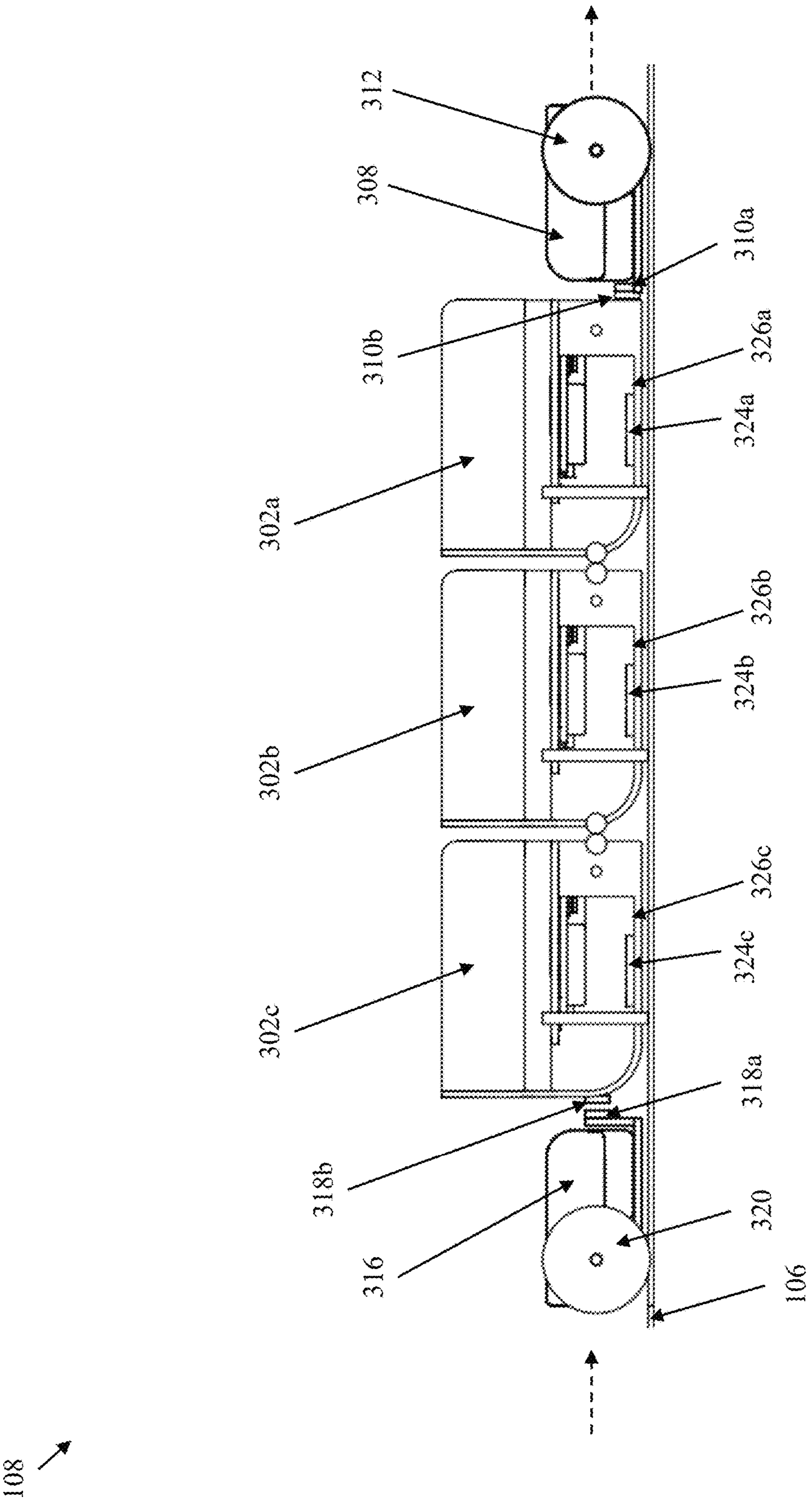

FIGS. 3A and 3B are schematic diagrams that illustrate an isometric view and a side view of the robot 108, respectively, consistent with disclosed embodiments of the present disclosure. The robot 108 is explained in conjunction with the FIGS. 3A and 3B.

The robot 108 may be configured to navigate on the track 106 (shown in FIGS. 3A and 3B). The robot 108 may include control modules 302*a*-302*c* (shown in FIGS. 3A and 3B). The control modules 302*a*-302*c* may be collectively referred to as the "set of control modules 302". The control modules 302*a*-302*c* may be magnetically coupled in series. For example, as shown in FIG. 3A, the control module 302*a* may include a magnet 304*a*, the control module 302*b* may include magnets 304*b* and 304*c*, and the control module 302*c* may include a magnet 304*d*. Further, the magnet 304*a* may be coupled to the magnet 304*b*, thereby magnetically coupling the control module 302*a* to the control module 302*b*. Further, the magnet 304*c* may be coupled to the magnet 304*d*, thereby magnetically coupling the control module 302*b* to the control module 302*c*. The magnetic coupling between the control modules 302*a*-302*c* may correspond to a magnetic attraction. In other words, the magnets 304*a* and 304*b* may have opposite polarities. Similarly, the magnets 304*c* and 304*d* may have opposite polarities. In an embodiment, the magnets 304*a*-304*d* may be cylindrical magnets. In an embodiment, the magnets 304*a*-304*d* may be permanent magnets or electromagnets. The magnets 304*a*-304*d* are shown but not labeled in FIG. 3B to keep the illustration concise and clear and should not be considered a limitation of the present disclosure.

The robot 108 may further include a puller module 308 (shown in FIGS. 3A and 3B). The puller module 308 may be magnetically coupled to the control modules 302*a*-302*c*. More specifically, the control module 302*a* may be magnetically coupled to the puller module 308. As illustrated in FIG. 3B, the puller module 308 may include a magnet 310*a* and the control module 302*a* may include a magnet 310*b*. In an embodiment, the magnet 310*b* may be on the opposite side to the magnet 304*a*. The magnet 310*a* may be magnetically coupled to the magnet 310*b*, thereby magnetically coupling the puller module 308 and the control module 302*a*. In an embodiment, the magnetic coupling between the control module 302*a* and the puller module 308 may correspond to a magnetic attraction. In other words, the magnets 310*a* and 310*b* may have opposite polarities. In an embodiment, the magnets 310*a* and 310*b* may be block magnets. In an embodiment, the magnets 310*a* and 310*b* may be permanent magnets or electromagnets. Although FIG. 3B shows one magnet each for the control module 302*a* and the puller module 308, the scope of the present disclosure is not limited to it. In several embodiments, the control module 302*a* may be coupled to the puller module 308 by way of multiple magnets of opposite polarities. For example, the control module 302*a* may be coupled to the puller module 308 by way of another pair of magnets similar to the magnets 310*a* and 310*b* positioned on the same side but at some distance from the magnets 310*a* and 310*b*.

The puller module 308 may be configured to pull the control modules 302*a*-302*c* along the track 106. In an embodiment, the puller module 308 may further include a first set of wheels 312 (shown in FIGS. 3A and 3B) and a first set of motors 314 (shown in FIG. 3A). In an embodiment, the first set of motors 314 may correspond to direct-current (DC) motors. The first set of motors 314 may be configured to drive the first set of wheels 312 along the track 106. Based on the driving of the first set of wheels 312 and the magnetic coupling of the magnet 310*a* to the control module 302*a* (e.g., to the magnet 310*b*), the control modules 302*a*-302*c* may be pulled along the track 106. In other words, the first set of motors 314 may drive the puller module 308, and the magnetic attraction between the magnets 310*a* and 310*b* may pull the control module 302*a* along the track 106. Additionally, the magnetic attraction between the magnets 304*a* and 304*b* and the magnets 304*c* and 304*d* may further pull the control modules 302*b* and 302*c* along the track 106, respectively.

To further facilitate the navigation of the robot 108, the robot 108 may further include a pusher module 316 (shown in FIGS. 3A and 3B). The pusher module 316 may be magnetically coupled to the control modules 302*a*-302*c*. More specifically, the control module 302*c* may be magnetically coupled to the pusher module 316. As illustrated in FIG. 3B, the pusher module 316 may include a magnet 318*a* and the control module 302*c* may include a magnet 318*b*. In an embodiment, the magnet 318*b* may be on the opposite side to the magnet 304*d*. The magnet 318*b* may be magnetically coupled to the magnet 318*a*, thereby magnetically coupling the pusher module 316 and the control module 302*c*. In an embodiment, the magnetic coupling between the control module 302*c* and the pusher module 316 may correspond to a magnetic repulsion. In other words, the magnets 318*a* and 318*b* may have the same polarities. In an embodiment, the magnets 318*a* and 318*b* may be block magnets. In an embodiment, the magnets 318*a* and 318*b* may be permanent magnets or electromagnets. Although FIG. 3B shows one magnet each for the control module 302*c* and the pusher module 316, the scope of the present disclosure is not limited to it. In several embodiments, the control module 302*c* may be coupled to the pusher module 316 by way of multiple magnets of the same polarities. For example, the control module 302*c* may be coupled to the pusher module 316 by way of another pair of magnets similar to the magnets 318*a* and 318*b* positioned on the same side but at some distance from the magnets 318*a* and 318*b*.

The pusher module 316 may be configured to push the control modules 302*a*-302*c* along the track 106. In an embodiment, the pusher module 316 may further include a second set of wheels 320 (shown in FIGS. 3A and 3B) and a second set of motors 322 (shown in FIG. 3A). In an embodiment, the second set of motors 322 may correspond to DC motors. The second set of motors 322 may be configured to drive the second set of wheels 320 along the track 106. Based on the driving of the second set of wheels 320 and the magnetic coupling of the magnet 318*a* to the control module 302*c* (e.g., to the magnet 318*b*), the control modules 302*a*-302*c* may be pushed along the track 106. In other words, the second set of motors 322 may drive the pusher module 316, and the magnetic repulsion between the magnets 318*a* and 318*b* may push the control module 302*c* along the track 106. Additionally, the magnetic attraction between the magnets 304*c* and 304*d* and the magnets 304*a* and 304*b* may further push the control modules 302*b* and 302*a* along the track 106, respectively.

The pull-push movements from the puller module 308 and the pusher module 316 may thus result in the navigation of the robot 108 along the track 106. The direction of the navigation of the robot 108 is shown in FIGS. 3A and 3B by way of dotted arrows. Thus, the puller module 308 and the pusher module 316 may be responsible for locomotion of the robot 108. The robot 108 may navigate along the track 106 based on the magnetic attraction between the magnets 310*a* and 310*b* (e.g., the magnetic attraction between the puller module 308 and the control module 302*a*), the magnetic attraction between the magnets 304*a*-304*d* (e.g., the magnetic attraction between the control modules 302*a*-302*c*), and the magnetic repulsion between the magnets 318*a* and 318*b* (e.g., the magnetic repulsion between the control module 302*c* and the pusher module 316). In an embodiment, the first and second sets of motors 314 and 322 may generate a differential drive to facilitate the navigation of the robot 108 along the track 106.

In an embodiment, the robot 108 may navigate along the track 106 based on a closure of the door 204. In other words, the movement of the robot 108 may be controlled based on the door 204, and every time the door 204 closes, the robot 108 may start navigating along the track 106 and may complete the entire circuit capturing images of various objects from different angles. In another embodiment, the robot 108 may navigate along the track 106 based on a weight change event associated with the physical space. In such cases, the refrigerator 102 may include a weight sensor (not shown) that may be configured to capture a total weight of objects inside the refrigerator 102. Whenever there is a change in the weight, the robot 108 may start navigating along the track 106 and may complete the entire circuit capturing images of various objects from different angles. This prevents the movement of the robot 108 in scenarios where the door 204 is opened and closed by the user without changing anything inside the refrigerator 102. In yet another embodiment, the robot 108 may navigate along the track 106 based on a lapse of a predefined time interval. In other words, the robot 108 may navigate along the track 106 periodically (e.g., daily, weekly, or the like). In yet another embodiment, the robot 108 may navigate along the track 106 based on a third user request.

Further, as illustrated in FIG. 3B, each of the control modules 302*a*-302*c* may include a magnet mounted on a base of a corresponding control module. For example, the control modules 302*a*-302*c* may include magnets 324*a*-324*c* mounted on bases 326*a*-326*c*, respectively. In an embodiment, the magnets 324*a*-324*c* may correspond to disk magnets. In an embodiment, the magnets 324*a*-324*c* may correspond to permanent magnets or electromagnets. Each of the magnets 324*a*-324*c* may facilitate the alignment of the corresponding control module of the control modules 302*a*-302*c* along the track 106 during the navigation of the robot 108. The control modules 302*a*-302*c* may not have active locomotion.

In several embodiments, the track 106 may include a conductive rail. In such cases, the puller module 308 and the pusher module 316 may include first and second sets of pogo pins 328 and 330 (shown in FIG. 3A), respectively. The first and second sets of pogo pins 328 and 330 may be mounted on the bottom or sides of the puller module 308 and the pusher module 316, respectively. A pogo pin may correspond to a small spring-loaded contact. The first set of pogo pins 328 may be coupled to the track 106 and a set of components (e.g., the first set of motors 314 and/or the magnet 310*a*) of the puller module 308. Further, the first set of pogo pins 328 may be configured to draw power from the track 106 and supply the drawn power to the set of components of the puller module 308. Similarly, the second set of pogo pins 330 may be coupled to the track 106 and a set of components (e.g., the second set of motors 322 and/or the magnet 318*a*) of the pusher module 316. Further, the second set of pogo pins 330 may be configured to draw power from the track 106 and supply the drawn power to the set of components of the pusher module 316. The first and second sets of pogo pins 328 and 330 may thus facilitate the navigation of the robot 108 inside the refrigerator 102.

As described in FIG. 1, while navigating along the track 106, the robot 108 (e.g., the control modules 302*a*-302*c*) may be configured to capture the input dataset. The input dataset may include a plurality of images associated with each of a plurality of objects (e.g., the objects 208*a*-208*c*) present in the physical space. The 3D representation of the physical space is derived based on the input dataset. The input dataset is not limited to including the images and is a function of the types of sensors included therein. The control module 302*a* is explained further in FIG. 4.

Although it is described that the robot 108 includes three control modules (e.g., the control modules 302*a*-302*c*), the scope of the present disclosure is not limited to it. In several embodiments, the robot 108 may include less than or more than three control modules, without deviating from the scope of the present disclosure.

The magnetic coupling of the modules may allow easy insertion and removal of modules. Upgrades to the robot 108 may thus be implemented in a simple and cost-effective manner. Further, if a control module is non-operational, it can be removed or replaced easily, minimizing downtime. Additionally, the puller and pusher modules 308 and 316 are self-contained, so repairs to the drive systems do not require disassembling the entire chain. As the control modules 302*a*-302*c* do not require wheels or motors, the design is simplified and potential failure points are reduced. Since all the modules are magnetically coupled rather than rigidly linked, the robot 108 may smoothly navigate small curves or uneven rails. The train-like format can conform better to small spaces inside the refrigerator 102. The power consumed by the robot 108 is minimal, as only the puller and pusher modules 308 and 316 require motors for locomotion, whereas the control modules 302*a*-302*c* are passively moved, drawing only enough power for sensing and communication.

Figure 4:
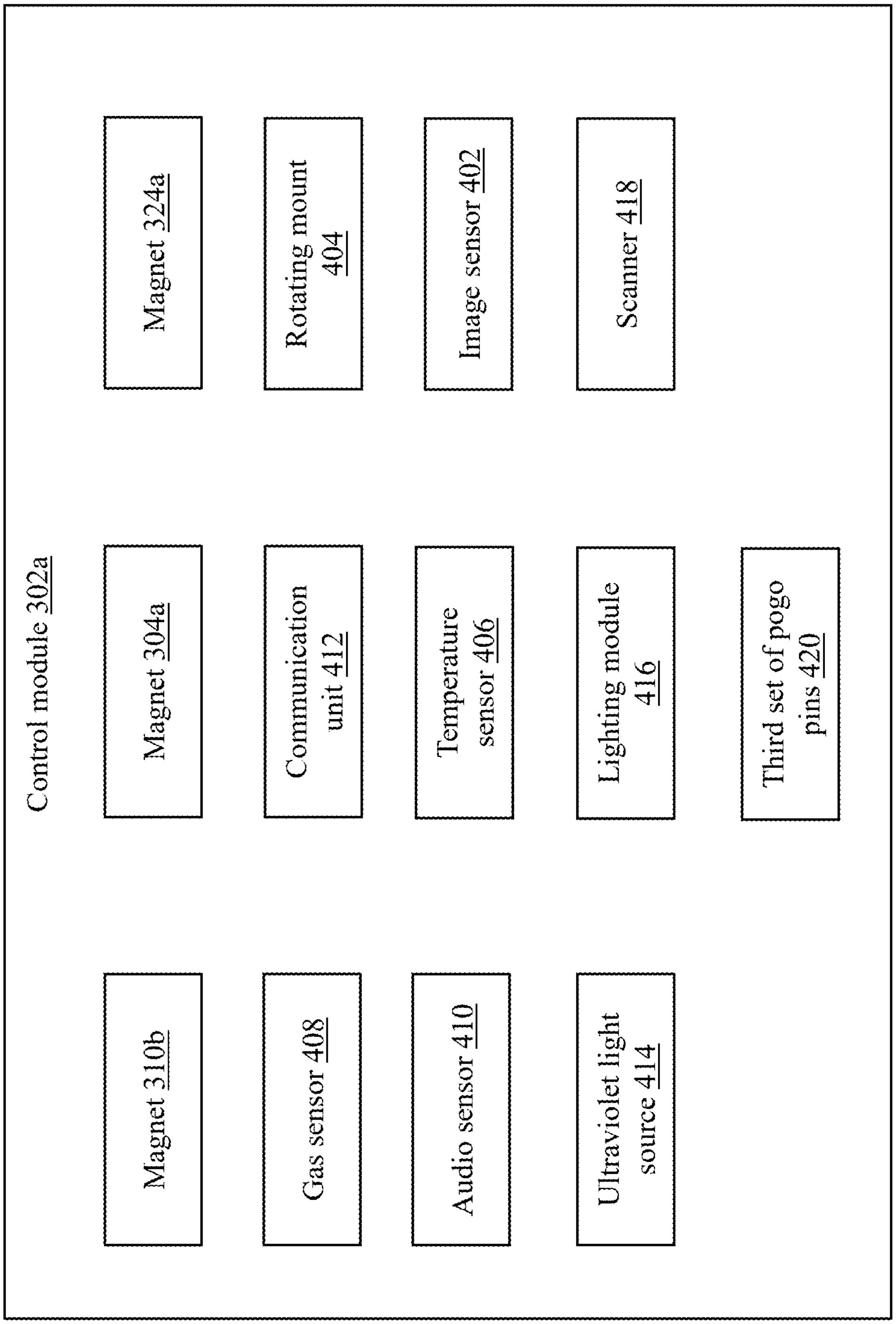
FIG. 4 is a block diagram of a control module of the robot, consistent with disclosed embodiments of the present disclosure.

FIG. 4 is a block diagram of a control module of the robot 108, consistent with disclosed embodiments of the present disclosure. The control module 302*a* is described in FIG. 4. However, other control modules (e.g., the control modules 302*b* and 302*c*) may be structurally similar to the control module 302*a*.

The control module 302*a* may include the magnets 304*a*, 310*b*, and 324*a*. The functionalities of the magnets 304*a*, 310*b*, and 324*a* are described above in FIGS. 3A and 3B. The control module 302*a* may further include one or more sensors that may be configured to generate sensing data. The input dataset may include the sensing data generated by the one or more sensors of each of the control modules 302*a*-302*c*.

In an embodiment, the one or more sensors may include an image sensor 402. The image sensor 402 may be configured to capture a set of images associated with each of a plurality of objects present in the physical space inside the refrigerator 102. The input dataset may thus include the set of images captured by the image sensors (such as the image sensor 402) of the control modules 302*a*-302*c*. In an example, the image sensor 402 may correspond to a wideangle high-resolution camera. In an embodiment, the control module 302*a* may include a rotating mount 404, and the image sensor 402 may be mounted on the rotating mount 404. Such an arrangement may ensure that the image sensor 402 can be rotated as the robot 108 navigates along the track 106, thereby capturing the images from various angles.

Although the control module 302*a* is shown to include a single image sensor (e.g., the image sensor 402), the scope of the present disclosure is not limited to it. In several embodiments, the control module 302*a* may include more than one image sensor, without deviating from the scope of the present disclosure.

The one or more sensors may further include a temperature sensor 406. The temperature sensor 406 may be configured to capture temperature sensing data indicative of a temperature of the physical space. In an embodiment, the temperature sensor 406 may correspond to a thermal camera that may monitor and map temperature distribution in the physical space. The temperature sensing data may be utilized to ensure that the temperature is maintained evenly throughout the housing 104.

The one or more sensors may further include a gas sensor 408. The gas sensor 408 may be configured to capture gas sensing data indicative of the air quality of the physical space. In an embodiment, the gas sensor 408 may be configured to detect gases like carbon dioxide, nitrogen, or the like, to monitor the air quality in the physical space.

The one or more sensors may further include an audio sensor 410. The audio sensor 410 may be configured to capture audio sensing data indicative of acoustic characteristics of the physical space. The audio sensor 410 may be employed to detect unusual noises, for example, fan issues, mechanical rattles within the physical space, or the like. In an example, the audio sensor 410 may correspond to a microphone.

The sensing data may thus include the temperature sensing data, the gas sensing data, and the audio sensing data. The temperature sensing data, the gas sensing data, and the audio sensing data may be utilized to generate the 3D representation of the physical space. Additionally or alternatively, the temperature sensing data, the gas sensing data, and the audio sensing data may be utilized to monitor the plurality of objects inside the refrigerator 102 and the internal conditions of the refrigerator 102.

Although the control module 302*a* is shown to include one temperature sensor, one gas sensor, and one audio sensor (e.g., the temperature sensor 406, the gas sensor 408, and the audio sensor 410), the scope of the present disclosure is not limited to it. In several embodiments, the control module 302*a* may include more than one temperature sensor, more than one gas sensor, and/or more than one audio sensor, without deviating from the scope of the present disclosure.

The control module 302*a* may further include a communication unit 412 that may be communicatively coupled to the one or more sensors (e.g., the image sensor 402, the temperature sensor 406, the gas sensor 408, and the audio sensor 410) and the processing device 110. The processing device 110 may thus be communicatively coupled to the control modules 302*a*-302*c* of the robot 108 by way of the communication unit 412. The communication unit 412 may be configured to facilitate communication of the sensing data to one or more components that are external to the robot 108. In other words, the communication unit 412 may be configured to facilitate communication of the sensing data to the processing device 110. In an embodiment, the communication unit 412 may correspond to a short-range radio-frequency unit, a Bluetooth unit, a Wireless fidelity (Wi-Fi) unit, or the like.

The scope of the present disclosure is not limited to the communication unit 412 being a wireless unit. In several embodiments, the communication unit 412 may correspond to a wired unit that may facilitate communication by way of the track 106 using one or more communication protocols.

The control module 302*a* may further include an ultraviolet light source 414. The ultraviolet light source 414 may be configured to sanitize the housing 104 (e.g., the interior of the refrigerator 102). The ultraviolet light source 414 may be utilized to kill bacteria, viruses, or the like, to disinfect the interior of the refrigerator 102.

The control module 302*a* may further include a lighting module 416. The lighting module 416 may be configured to provide additional illumination inside the refrigerator 102 for better imaging or visibility. In other words, the lighting module 416 may facilitate the capturing of clearer images of the physical space inside the refrigerator 102. In some embodiments, the lighting module 416 may also serve as an indicator module for conveying alerts or status signals. In an embodiment, the lighting module 416 may correspond to a light-emitting diode (LED), an infrared light source, a laser light source, an incandescent bulb, or the like.

The control module 302*a* may further include a scanner 418. The scanner 418 may be configured to scan and identify items (e.g., food packages). The scanner 418 may be utilized in integration with a smart inventory management system.

In several embodiments, the track 106 may include a conductive rail. In such cases, the control module 302*a* may include a third set of pogo pins 420. The third set of pogo pins 420 may be mounted on the bottom or sides of the control module 302*a*. The third set of pogo pins 420 may be coupled to the track 106 and a set of components (e.g., the magnets 304*a*, 310*b*, and 324*a*, the one or more sensors, the communication unit 412, the ultraviolet light source 414, the lighting module 416, and/or the scanner 418) of the control module 302*a*. Further, the third set of pogo pins 420 may be configured to draw power from the track 106 and supply the drawn power to the set of components of the control module 302*a*.

Although it is described that the control modules 302*b* and 302*c* are similar to the control module 302*a*, the scope of the present disclosure is not limited to it. In numerous embodiments, each of the control modules 302*a*-302*c* may include different types of sensors, without deviating from the scope of the present disclosure. For example, the control module 302*a* may include an image sensor (such as the image sensor 402), the control module 302*b* may include a temperature sensor (such as the temperature sensor 406), and the control module 302*c* may include a gas sensor (such as the gas sensor 408).

Figure 5:
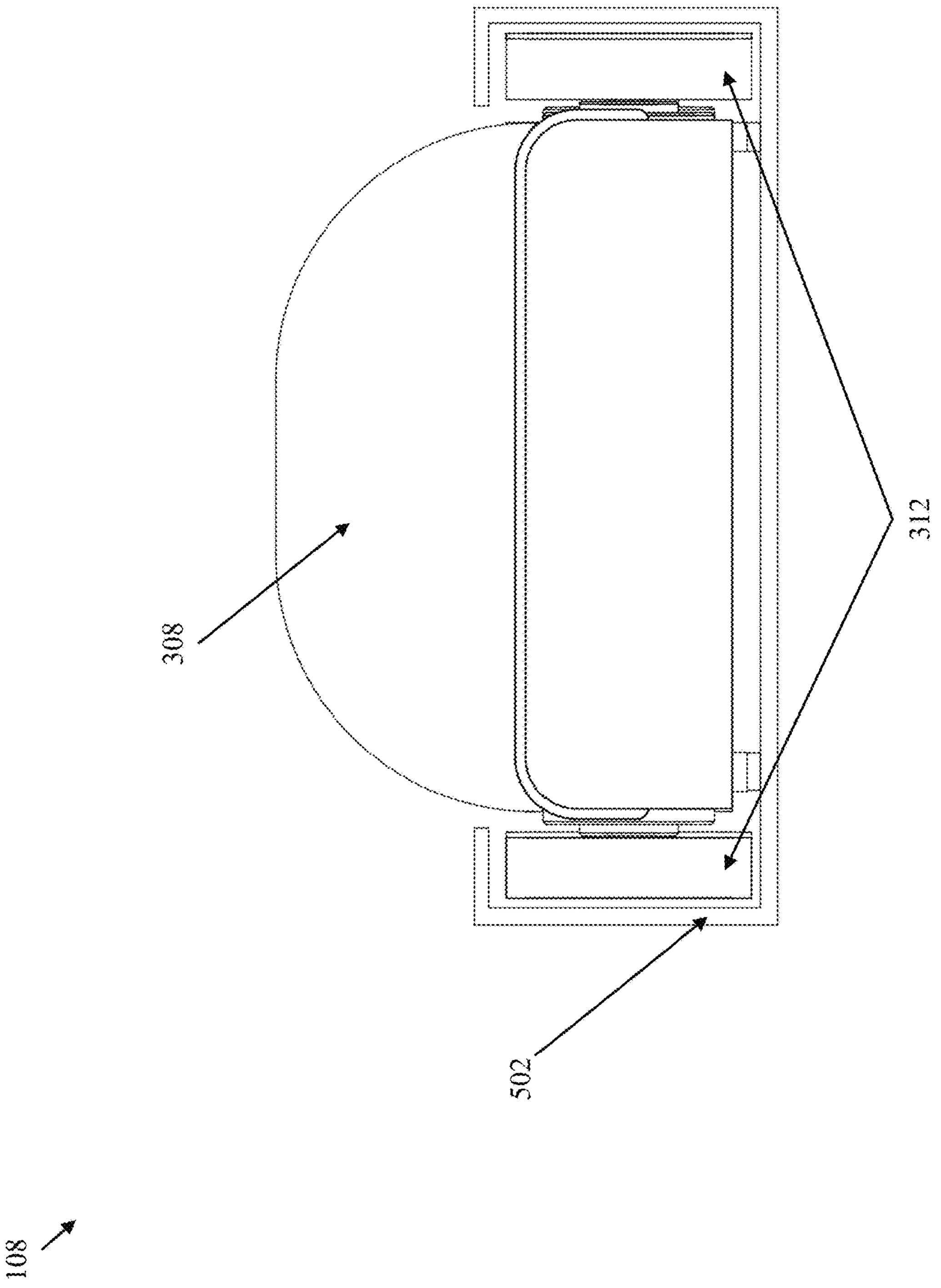
FIG. 5 is a schematic diagram that illustrates a front view of the robot, consistent with disclosed embodiments of the present disclosure.

FIG. 5 is a schematic diagram that illustrates a front view of the robot 108, consistent with disclosed embodiments of the present disclosure. As illustrated in FIG. 5, the robot 108 may navigate on a track 502. The track 502 illustrated in FIG. 5 is different from the track 106 illustrated in FIGS. 2A, 2B, 3A, and 3B. The track 502 illustrated in FIG. 5 provides an enclosed structure where the first set of wheels 312 can move within the track 106. The robot 108 (e.g., the first set of wheels 312) may thus be configured to navigate within the track 502, which is different from the track 106 illustrated in FIGS. 2A, 2B, 3A, where the first set of wheels 312 move on the track 106. Such an enclosed structure may ensure that the robot 108 (e.g., the first set of wheels 312) moves in a steady manner.

Figure 6:
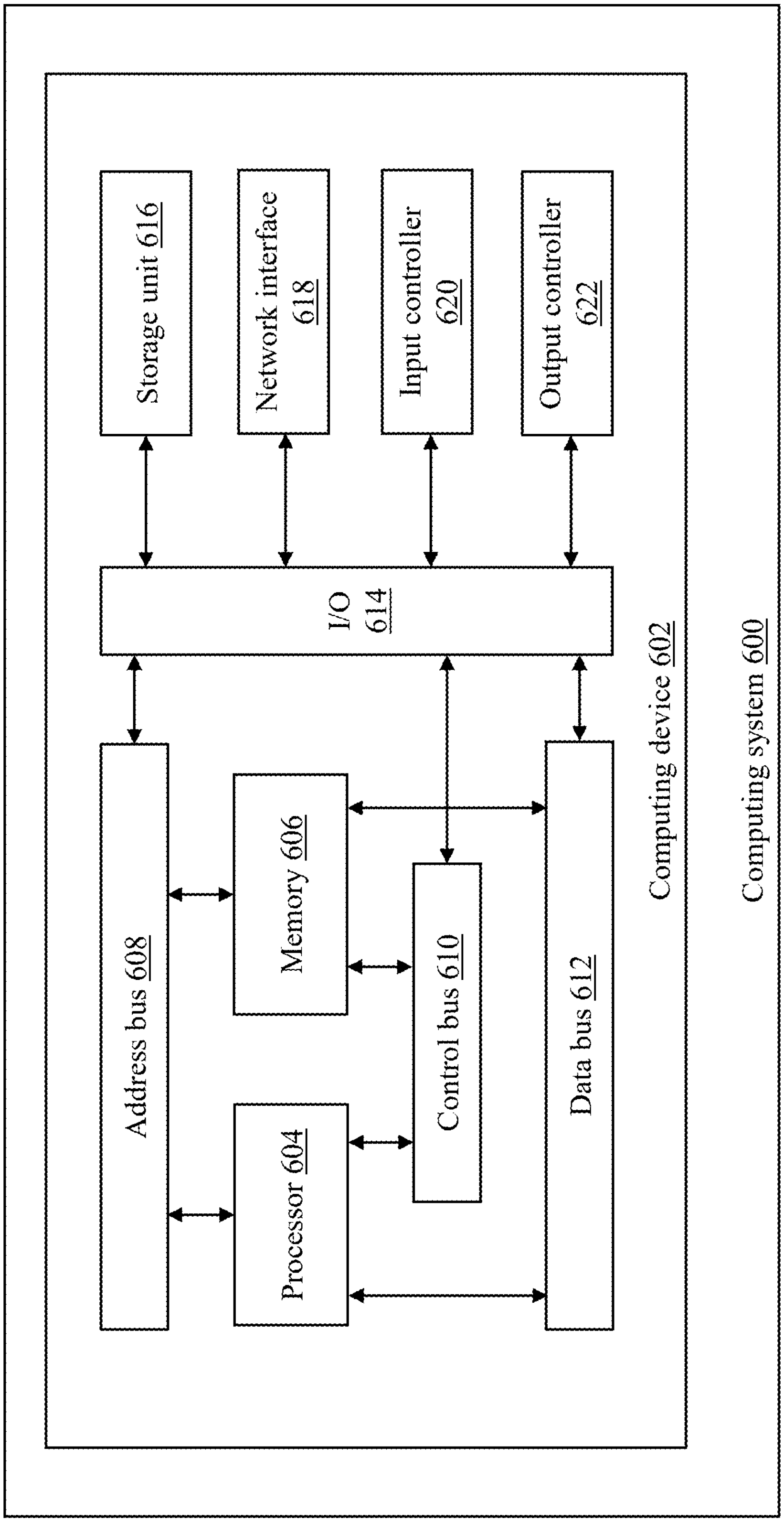
FIG. 6 shows an example computing system for carrying out the methods of the present disclosure, consistent with disclosed embodiments of the present disclosure.

FIG. 6 shows an example computing system 600 for carrying out the operations of the present disclosure, consistent with disclosed embodiments of the present disclosure. Specifically, FIG. 6 shows a block diagram of an embodiment of the computing system 600 according to example embodiments of the present disclosure.

The computing system 600 may be configured to perform any of the operations disclosed herein. The computing system 600 may be implemented as a conventional computer system, an embedded controller, a laptop, a server, a mobile device, a smartphone, a customized machine, any other hardware platform, or any combination or multiplicity thereof. In one embodiment, the computing system 600 is a distributed system configured to function using multiple computing machines interconnected via a data network or bus system.

The computing system 600 includes computing devices (such as a computing device 602). The computing device 602 includes one or more processors (such as a processor 604) and a memory 606. The processor 604 may be any general-purpose processor(s) configured to execute a set of instructions. For example, the processor 604 may be a processor core, a multiprocessor, a reconfigurable processor, a microcontroller, a digital signal processor (DSP), an application-specific integrated circuit (ASIC), a graphics processing unit (GPU), a neural processing unit (NPU), an accelerated processing unit (APU), a brain processing unit (BPU), a data processing unit (DPU), a holographic processing unit (HPU), an intelligent processing unit (IPU), a microprocessor/microcontroller unit (MPU/MCU), a radio processing unit (RPU), a tensor processing unit (TPU), a vector processing unit (VPU), a wearable processing unit (WPU), a field programmable gate array (FPGA), a programmable logic device (PLD), a controller, a state machine, gated logic, discrete hardware component, any other processing unit, or any combination or multiplicity thereof. In one embodiment, the processor 604 may be multiple processing units, a single processing core, multiple processing cores, special purpose processing cores, co-processors, or any combination thereof. The processor 604 may be communicatively coupled to the memory 606 via an address bus 608, a control bus 610, and a data bus 612.

The memory 606 may include non-volatile memories such as a read-only memory (ROM), a programable read-only memory (PROM), an erasable programmable read-only memory (EPROM), a flash memory, or any other device capable of storing program instructions or data with or without applied power. The memory 606 may also include volatile memories, such as a random-access-memory (RAM), a static random-access-memory (SRAM), a dynamic random-access-memory (DRAM), and a synchronous dynamic random-access-memory (SDRAM). The memory 606 may include single or multiple memory modules. While the memory 606 is depicted as part of the computing device 602, a person skilled in the art will recognize that the memory 606 may be separate from the computing device 602.

The memory 606 may store information that may be accessed by the processor 604. For instance, the memory 606 (e.g., one or more non-transitory computer-readable storage mediums, memory devices) may include computer-readable instructions (not shown) that may be executed by the processor 604. The computer-readable instructions may be software written in any suitable programming language or may be implemented in hardware. Additionally, or alternatively, the computer-readable instructions may be executed in logically and/or virtually separate threads on the processor 604. For example, the memory 606 may store instructions (not shown) that when executed by the processor 604 cause the processor 604 to perform operations such as any of the operations and functions for which the computing system 600 is configured, as described herein. Additionally, or alternatively, the memory 606 may store data (not shown) that may be obtained, received, accessed, written, manipulated, created, and/or stored. The data may include, for instance, the data and/or information described herein in relation to FIGS. 1-5. In some implementations, the computing device 602 may obtain from and/or store data in one or more memory device(s) that are remote from the computing system 600.

The computing device 602 may further include an input/output (I/O) interface 614 communicatively coupled to the address bus 608, the control bus 610, and the data bus 612. The data bus 612 may include a plurality of tunnels that may support communication in the environment 100. The I/O interface 614 is configured to couple to one or more external devices (e.g., to receive and send data from/to one or more external devices). Such external devices, along with the various internal devices, may also be known as peripheral devices. The I/O interface 614 may include both electrical and physical connections for operably coupling the various peripheral devices to the computing device 602. The I/O interface 614 may be configured to communicate data, addresses, and control signals between the peripheral devices and the computing device 602. The I/O interface 614 may be configured to implement any standard interface, such as a small computer system interface (SCSI), a serial-attached SCSI (SAS), a fiber channel, a peripheral component interconnect (PCI), a PCI express (PCIe), a serial bus, a parallel bus, an advanced technology attachment (ATA), a serial ATA (SATA), a universal serial bus (USB), Thunderbolt, FireWire, various video buses, and the like. The I/O interface 614 is configured to implement only one interface or bus technology. Alternatively, the I/O interface 614 is configured to implement multiple interfaces or bus technologies. The I/O interface 614 may include one or more buffers for buffering transmissions between one or more external devices, internal devices, the computing device 602, or the processor 604. The I/O interface 614 may couple the computing device 602 to various input devices, including touch screens, scanners, biometric readers, electronic digitizers, receivers, touchpads, cameras, keyboards, any other pointing devices, or any combinations thereof. The I/O interface 614 may couple the computing device 602 to various output devices, including printers, projectors, tactile feedback devices, automation control, robotic components, actuators, transmitters, signal emitters, lights, and so forth.

The computing system 600 may further include a storage unit 616, a network interface 618, an input controller 620, and an output controller 622. The storage unit 616, the network interface 618, the input controller 620, and the output controller 622 are communicatively coupled to the central control unit (e.g., the memory 606, the address bus 608, the control bus 610, and the data bus 612) via the I/O interface 614. The network interface 618 communicatively couples the computing system 600 to one or more networks such as wide area networks (WAN), local area networks (LAN), intranets, the Internet, wireless access networks, wired networks, mobile networks, telephone networks, optical networks, or combinations thereof. The network interface 618 may facilitate communication with packet-switched networks or circuit-switched networks which use any topology and may use any communication protocol. Communication links within the network may involve various digital or analog communication media such as fiber optic cables, free-space optics, waveguides, electrical conductors, wireless links, antennas, radio-frequency communications, and so forth.

The storage unit 616 is a computer-readable medium, preferably a non-transitory computer-readable medium, comprising one or more programs, the one or more programs comprising instructions which when executed by the processor 604 cause the computing system 600 to perform the method steps of the present disclosure. Alternatively, the storage unit 616 is a transitory computer-readable medium. The storage unit 616 may include a hard disk, a floppy disk, a compact disc read-only memory (CD-ROM), a digital versatile disc (DVD), a Blu-ray disc, a magnetic tape, a flash memory, another non-volatile memory device, a solid-state drive (SSD), any magnetic storage device, any optical storage device, any electrical storage device, any semiconductor storage device, any physical-based storage device, any other data storage device, or any combination or multiplicity thereof. In one embodiment, the storage unit 616 stores one or more operating systems, application programs, program modules, data, or any other information. The storage unit 616 is part of the computing device 602. Alternatively, the storage unit 616 is part of one or more other computing machines that are in communication with the computing device 602, such as servers, database servers, cloud storage, network attached storage, and so forth.

The input controller 620 may include suitable logic, circuitry, interfaces, and/or code, executable by the circuitry, that may be configured to control one or more input devices that may be configured to receive user requests. The output controller 622 may include suitable logic, circuitry, interfaces, and/or code, executable by the circuitry, that may be configured to control one or more output devices that may be configured to output 3D representations and object details.

A person of ordinary skill in the art will appreciate that embodiments and exemplary scenarios of the disclosed subject matter may be practiced with various computer system configurations, including multi-core multiprocessor systems, minicomputers, mainframe computers, computers linked or clustered with distributed functions, as well as pervasive or miniature computers that may be embedded into virtually any device. Further, the operations may be described as a sequential process, however, some of the operations may be performed in parallel, concurrently, and/or in a distributed environment, and with program code stored locally or remotely for access by single or multiprocessor machines. In addition, in some embodiments, the order of operations may be rearranged without departing from the spirit of the disclosed subject matter.

Techniques consistent with the present disclosure provide, among other features, systems for 3D reconstruction of the interiors of closed containers. While various embodiments of the disclosed systems and methods have been described above, they have been presented for purposes of example only, and not limitations. It is not exhaustive and does not limit the present disclosure to the precise form disclosed. Modifications and variations are possible considering the above teachings or may be acquired from practicing the present disclosure, without departing from the breadth or scope.

What is claimed is:

1. A robot, comprising:

a set of control modules;

a puller module that is magnetically coupled to the set of control modules, and configured to pull the set of control modules along a track that is mounted on a plurality of walls of a housing encompassing a physical space; and a pusher module that is magnetically coupled to the set of control modules, and configured to push the set of control modules along the track, wherein while navigating along the track, the set of control modules is configured to capture an input dataset, wherein the input dataset comprises a plurality of images associated with each of a plurality of objects present in the physical space, and wherein a three-dimensional (3D) representation of the physical space is derived based on the input dataset.

2. A system, comprising:

a housing encompassing a physical space, wherein the housing comprises a plurality of walls;

a track mounted on the plurality of walls; and a robot configured to navigate along the track, wherein the robot comprises:

a set of control modules;

a puller module that is magnetically coupled to the set of control modules, and configured to pull the set of control modules along the track; and a pusher module that is magnetically coupled to the set of control modules, and configured to push the set of control modules along the track, wherein while navigating along the track, the set of control modules is configured to capture an input dataset, wherein the input dataset comprises a plurality of images associated with each of a plurality of objects present in the physical space, and wherein a three-dimensional (3D) representation of the physical space is derived based on the input dataset.

3. The system of claim 2, wherein the track corresponds to a continuous rail mounted on the plurality of walls in a horizontal direction and a vertical direction.

4. The system of claim 2, wherein the housing further comprises a set of trays arranged within the physical space in contact with the plurality of walls, wherein the plurality of objects are positioned on the set of trays, and wherein the track is further mounted on a bottom surface of at least one of the set of trays.

5. The system of claim 2, wherein the set of control modules comprises a first control module, a second control module, and a third control module that are magnetically coupled in series, wherein the first control module is further magnetically coupled to the puller module, and wherein the third control module is further magnetically coupled to the pusher module.

6. The system of claim 2, wherein each of the set of control modules comprises a magnet mounted on a base of a corresponding control module, and wherein the magnet facilitates alignment of each of the set of control modules along the track during the navigation of the robot.

7. The system of claim 2, wherein the puller module comprises (i) a first set of wheels, (ii) a first set of motors configured to drive the first set of wheels along the track, and (iii) a first set of magnets that is magnetically coupled to a first control module of the set of control modules, wherein based on the driving of the first set of wheels and the magnetic coupling of the first set of magnets to the first control module, the set of control modules is pulled along the track, wherein the pusher module comprises (i) a second set of wheels, (ii) a second set of motors configured to drive the second set of wheels along the track, and (iii) a second set of magnets that is magnetically coupled to a second control module of the set of control modules, and wherein based on the driving of the second set of wheels and the magnetic coupling of the second set of magnets to the second control module, the set of control modules is pushed along the track.

8. The system of claim 2, wherein the puller module comprises a first set of magnets, wherein the pusher module comprises a second set of magnets, wherein the set of control modules comprises (i) a first control module that comprises a third set of magnets that is magnetically coupled to the first set of magnets, and (ii) a second control module that comprises a fourth set of magnets that is magnetically coupled to the second set of magnets, and wherein the robot navigates along the track based on (i) a magnetic attraction between the first set of magnets and the third set of magnets and (ii) a magnetic repulsion between the second set of magnets and the fourth set of magnets.

9. The system of claim 2, wherein the track comprises a conductive rail, and wherein each of the set of control modules, the puller module, and the pusher module comprises (i) a set of components and (ii) a set of pogo pins that is coupled to the track and the set of components, and configured to draw power from the track and supply the drawn power to the set of components.

10. The system of claim 2, wherein each of the set of control modules comprises:

one or more sensors configured to generate sensing data, wherein the input dataset comprises the sensing data generated by the one or more sensors of each of the set of control modules; and a communication unit that is communicatively coupled to the one or more sensors, and configured to facilitate communication of the sensing data to one or more components that are external to the robot.

11. The system of claim 10, wherein the one or more sensors comprise an image sensor configured to capture a set of images of the plurality of images.

12. The system of claim 11, wherein each of the set of control modules further comprises a rotating mount, and wherein the image sensor is mounted on the rotating mount.

13. The system of claim 10, wherein the one or more sensors, of each of the set of control modules, comprise at least one of:

a temperature sensor configured to capture temperature sensing data indicative of a temperature of the physical space, a gas sensor configured to capture gas sensing data indicative of air quality of the physical space, or an audio sensor configured to capture audio sensing data indicative of acoustic characteristics of the physical space.

14. The system of claim 2, wherein each of the set of control modules comprises an ultraviolet light source that is configured to sanitize the housing.

15. The system of claim 2, further comprising a processing device that is communicatively coupled to the set of control modules, and configured to:

obtain the input dataset;

process the input dataset to determine the plurality of objects present in the physical space; and generate, using a 3D reconstruction model, the 3D representation of the physical space based on the processed input dataset.

16. The system of claim 15, wherein the 3D reconstruction model is trained based on a training dataset that comprises one or more images of one or more objects, respectively, that are associated with the system.

17. The system of claim 15, wherein the processing device is further configured to:

receive, from a user device, a user request that is indicative of visualization of the plurality of objects, wherein the processing device generates the 3D representation of the physical space in response to the user request; and render the 3D representation of the physical space on the user device.

18. The system of claim 15, wherein to generate the 3D representation of the physical space, the processing device is further configured to:

detect, from the plurality of objects, at least a first object that is occluded; and reconstruct the first object using the 3D reconstruction model.

19. The system of claim 2, wherein the housing further comprises a door enclosing the plurality of walls, and wherein the robot navigates along the track based on one of (i) a closure of the door, (ii) a weight change event associated with the physical space, (iii) a lapse of a predefined time interval, or (iv) a user request.

20. The system of claim 2, wherein the track is mounted on the plurality of walls such that based on the navigation along the track, the robot is configured to capture an entire scene of the physical space.

* * * * *